US011299508B2

(12) United States Patent
Padilla-Acevedo et al.

(10) Patent No.: US 11,299,508 B2
(45) Date of Patent: Apr. 12, 2022

(54) SYNTHESIS OF CYCLIC ORGANIC COMPOUNDS AND METALLOCENES

(71) Applicant: Univation Technologies, LLC, Houston, TX (US)

(72) Inventors: Angela I. Padilla-Acevedo, Lake Jackson, TX (US); Roger L. Kuhlman, Lake Jackson, TX (US)

(73) Assignee: Univation Technologies, LLC, Houston, TX (US)

( * ) Notice: Subject to any disclaimer, the term of this patent is extended or adjusted under 35 U.S.C. 154(b) by 108 days.

(21) Appl. No.: 16/649,934

(22) PCT Filed: Sep. 19, 2018

(86) PCT No.: PCT/US2018/051617
§ 371 (c)(1),
(2) Date: Mar. 23, 2020

(87) PCT Pub. No.: WO2019/067272
PCT Pub. Date: Apr. 4, 2019

(65) Prior Publication Data
US 2021/0163518 A1    Jun. 3, 2021

Related U.S. Application Data

(60) Provisional application No. 62/564,334, filed on Sep. 28, 2017.

(51) Int. Cl.
*C08F 4/6592* (2006.01)
*C07F 17/00* (2006.01)
*C07C 45/45* (2006.01)
*C07C 45/48* (2006.01)
*C08F 4/76* (2006.01)
*C08F 10/02* (2006.01)

(52) U.S. Cl.
CPC ............ *C07F 17/00* (2013.01); *C07C 45/455* (2013.01); *C07C 45/48* (2013.01); *C08F 4/65925* (2013.01); *C08F 4/76* (2013.01); *C08F 10/02* (2013.01)

(58) Field of Classification Search
CPC ..... C07F 17/00; C07F 4/65925; C07C 45/455
See application file for complete search history.

(56) References Cited

U.S. PATENT DOCUMENTS

| 5,721,185 A | 2/1998 | LaPointe et al. |
| 2004/0249096 A1 | 12/2004 | McCullough |
| 2006/0173123 A1 | 8/2006 | Yang et al. |

FOREIGN PATENT DOCUMENTS

| JP | 10316694 | 12/1998 |
| WO | 2016/168700 A1 | 10/2016 |
| WO | 2018064044 | 4/2018 |

OTHER PUBLICATIONS

Oliver Gobley et al., Organometallics, 1998, pp. 4897-4903, vol. 17, No. 22.
Asachenkon, New Zirconocenes with 4,5,6,7-tetrahydroindene ligands. Synthesis and Catalytic activity in the polymerization of ethylene with hex-1-ene, Russian Chemical Bulletin, 2017, vol. 65, No. 6, pp. 1580-1585.
Austin, Synthesis and Properties of Novel Substituted 4,5,6,7-tetrahydroindenes and Selected Metal Complexes, Journal of Organometallic Chemistry, 1995, vol. 491, No. 1-2, pp. 11-18.
Batsanov, Sterically Demanding Cyclopentadienyl Chemistry: Synthesis of Iron and Zirconium Complexes of 1-Phenyl-3-Methyl-4,5,6,7-Tetrahydroindenyl, Journal of Organometallic Chemistry, 1999, vol. 590, pp. 169-179.
Conia, Tetrahedron Letters, 1968, vol. 17, p. 2101.
Eaton, Phosphorus Pentoxide-Methanesulfonic Acid. A Convenient Alternative to Polyphosphoric Acid, Journal of Organic Chemistry, 1978, 38, 4071.
Jacob et al, Organic reactions with polyphosphoric acid. VI. Intramolecular acylation with lactones.
Nazarov, 3-Methyl-Tetrahydro-1-Pentalenone Neftekhimiya, 1965, vol. 5, No. 2, p. 177-183.
Paquette, Stereocontrolled Total Synthesis of the Triquinane Marine Sesquiterpene-Capnellene, Canadian Journal of Chemistry.1984, 62, 2415.
Paquette, Studies Directed Toward the Total Synthesis of Trixkingolide. Analysis of the Capacity for Transannular Carbon-Carbon Bond Formation in Various Bicyclic and Tricyclic Intermediates, J. Org. Chem. 1989, 54, 3334.
Polo, From Zirconium to Titanium: The Effect of the Metal in Propylene Polymerisation using Fluxional Unbridged Bicyclic Catalysts, Macromolecular Sympo, 2004,vol. 213, pp. 89-99.
Rand, Competitive Carbonium Ion Processes. Catalysis of Acylation and Acetoxylation Reactions by Polyphosphoric Acid, Journal of Organic Chemistry, 1966, 31, p. 4061.
Rand et al., The Acylation of Cycloheptene, Journal of Organic Chemistry, 1966, 31, p. 3063.
Schostarez et al., Highly stereocontrolled synthesis of propellane sesquiterpenes. 1981, vol. 37, No. 25 pp. 4431-4435.
Tabatabaenian, Synthesis and Spectroscopic Studies of New Substituted Dinuclear η5-4,5,6,7-Tetrahydroindenyl Rhuthenium Complexes. Russian Journal of Coordination Chemistry, 2003, vol. 29, No. 7, p. 501.

(Continued)

*Primary Examiner* — Caixia Lu

(57) ABSTRACT

A method comprising synthesizing a cyclic organic compound via reaction of an unsubstituted or substituted cyclopentene with an unsubstituted or substituted acrylic acid in the presence of phosphoric and/or sulfonic acid reagent to make the cyclic organic compound. Also, a method of synthesizing a ligand for a transition metal, and a related substituted ligand-metal complex and catalyst, from the unsubstituted or substituted cyclopentene and unsubstituted or substituted acrylic acid. Also, the cyclic organic compound, ligand, and substituted ligand-metal complex and catalyst synthesized thereby. Also a method of polymerizing an olefin with the catalyst to give a polyolefin, and the polyolefin made thereby.

10 Claims, No Drawings

(56) References Cited

OTHER PUBLICATIONS

Brancaccio, Farmaco, Edizione Scientifica, 1983, 9, 702-708.
Yokota, Consideration of Mechanism of Styrene/Ethylene Copolymerization with Half-Titanocene Catalysts, Journal of Polymer Science, 2005, 43, 5041.
Yoshio, Kenkyu Hokoku-Asahi Garasu Kogyo Gijutsu Shoreikai, 1986, vol. 49, 225-230.
Yoshio, Degradation of Polyethylene to Aromatic Hydrocarbons over metal-supported activated carbon catalysts, Journal of Analytical and Applied Pyrolysis, 1989, 14(4), 331-344.
Ouellette, Conformational Analysis. VIII.1,2 Relative Stabilities of 5-Cyanobicyclo[2.2.2]octenes and 5-Acetylbicyclo [2.2.2]octenes, 1966, p. 3065.

SYNTHESIS OF CYCLIC ORGANIC COMPOUNDS AND METALLOCENES

FIELD

Synthesizing cyclic organic compounds, and substituted metallocenes therefrom.

INTRODUCTION

Metallocene complexes comprise a transition metal atom that is bonded to two ligands independently selected from an unsubstituted cyclopentadienyl (Cp) ligand (formally an anion of formula $C_5H_5$) and/or a substituted cyclopentadienyl ligand, which is isolobal to Cp. The transition metal is an element of any one of Groups 3 to 12 useful for catalyzing polymerizations of olefins. Examples of the transition metal are Group 4 metals such as titanium, zirconium, and hafnium. Examples of the substituted cyclopentadienyl ligands are methylcyclopentadienyl and 4,5,6,7-tetrahydroindenyl. A typical metallocene complex is a 4,5,6,7-tetrahydroindenyl-cyclopentadienyl zirconium dimethyl complex ((4,5,6,7-tetrahydroindenyl)(cyclopentadienyl)Zr(CH$_3$)$_2$). Typically, the synthesis of the complex involves numerous synthetic steps, uses expensive reagents, and/or employs a platinum-catalyzed hydrogenation step to convert an indenyl-cyclopentadienyl zirconium dichloride compound to a 4,5,6,7-tetrahydroindenyl-cyclopentadienyl zirconium dichloride compound. See, e.g., US 2004/0249096 A1 and U.S. Pat. No. 5,721,185.

Uemichi, Yoshio; Kanoh, Hisao. *Kenkyu Hokoku-Asahi Garasu Kogyo Gijutsu Shoreikai*, Volume 49, Pages 225-30, 1986. CODEN:AGKGAA. ISSN:0365-2599 report that platinum is especially potent source of polyethylene degradation. Uemichi, Yoshio; Makino, Yutaka; Kanazuka, Takaji, *Degradation of polyethylene to aromatic hydrocarbons over metal-supported activated carbon catalysts*, Journal of Analytical and Applied Pyrolysis (1989), 14(4), 331-44.

See also the following. Tabatabaenian, K.; Mamaghani, M.; Neshat, A.; Masjedi, M. Synthesis and Spectroscopic Studies of New Substituted Dinuclear $\eta^5$-4,5,6,7-Tetrahydroindenyl Ruthenium Complexes. *Russian Journal of Coordination Chemistry.* 2003, 29, 7, 501. Austin, R. N.; Clark, T. J.; Dickson, T. E.; Killian, C. M.; Nile, T. A.; Shabacker, D. J.; McPhail, T. A. Synthesis and Properties of Novel Substituted 4,5,6,7-tetrahydroindenes and Selected Metal Complexes. *Journal of Organometallic Chemistry.* 1995, 491, 11. Conia, J. M.; Leriverend, M. L. *Tetrahedron Letters.* 1968, 17, 2101 (Conia et al.). L. Rand and R. J. Dolinski, *J. Org. Chem.*, 1966, 31, 3063 and L. Rand and R. J. Dolinski, *J. Org. Chem.*, 1966, 31, 4061 (collectively "Rand and Dolinski"). Yokota, K.; Kohsaka, T.; Ito, K.; Ishihara, N. Consideration of Mechanism of Styrene/Ethylene Copolymerization with Half-Titanocene Catalysts. *Journal of Polymer Science.* 2005, 43, 5041. JP10316694A to Tetsuya, I., et. al. Brancaccio G.; Lettieri, G.; Monforte, P.; Larizza, A. Farmaco, *Edizione Scientifica.* 1983, 9, 702-8. Eaton, P. E.; Carlson, G. R.; Lee, J. T. Phosphorus Pentoxide-Methanesulfonic Acid. A Convenient Alternative to Polyphosphoric Acid. *J. Org. Chem.* 1978, 38, 4071. Paquette, L. A.; Stevens, K. E., Can. J. Chem. 1984, 62, 2415. Paquette, L. A.; Cheney, D. L., *J. Org. Chem.* 1989, 54, 3334. *J. Org. Chem.* 1966, 3065.

Conia, et al. reported that reacting cyclohexene and crotonic acid in presence of polyphosphoric acid (PPA) exclusively gave as a sole product 2,3,4,5,6,7-hexahydro-3-methyl-1H-inden-1-one (structure 1 in Conia et al.). Conia et al. reported reacting cyclopentyl crotonate or cyclohexyl crotonate in the presence of PPA gave 3-methyl-bicyclo [3.3.0]-2-octen-1-one (40% yield, Table 1 in Conia et al.) or 2,3,4,5,6,7-hexahydro-3-methyl-1H-inden-1-one (60% yield, Table 2 in Conia et al.), respectively.

Rand and Dolinski use polyphosphoric acid (PPA) or a mixture of phosphorous pentoxide ($P_2O_5$ or $P_4O_{10}$) and PPA to catalyze the reaction of a cycloheptene, cyclohexene, or cyclopentene with an alpha,beta-unsaturated carboxylic acid such as acrylic acid or crotonic acid gives a reaction mixture that contains or is free of an ester by-product such as cycloheptyl crotonate, cyclohexyl crotonate, or cyclopentyl crotonate. Relatively how much of the ester by-product is made is said to depend on the amount of phosphorous pentoxide used in the mixture with PPA or the amount of the PPA or $P_2O_5$/PPA mixture relative to the amount of cycloalkene.

SUMMARY

We discovered an alternative shorter synthesis of an (unsubstituted or substituted)-tetrahydropentalenyl-metal dichloride complex that does not use a hydrogenation catalyst, a hydrogenation step, or a hydrogenation catalyst filtration step. The inventive (unsubstituted or substituted)-tetrahydropentalenyl-metal dichloride complex made thereby, and the inventive (unsubstituted or substituted)-tetrahydropentalenyl-metal dimethyl catalyst made therefrom, and polyolefins made therewith are beneficially free of (added) hydrogenation catalyst metals such as platinum, palladium, nickel, rhodium, and ruthenium. As discussed above, polyolefin degradation problems have been attributed to hydrogenation catalyst metals are reported in the literature, and thus the inventive polyolefin beneficially would inherently avoid any such problem(s). As such, the inventive polyolefin could have longer stability or less degradation than prior polyolefins made with a catalyst synthesized using a hydrogenation step. The instability or degradation could appear over a long period of time as discoloration and/or a change in molecular weight distribution of the polyolefin, or some other manifestation thereof.

The inventive method is applied to tetrahydropentalenyl systems and comprises synthesizing a cyclic organic compound via reaction of an unsubstituted or substituted cyclopentene with an unsubstituted or substituted acrylic acid in the presence of phosphoric and/or sulfonic acid reagent to make the cyclic organic compound. Also, a method of synthesizing a ligand for a transition metal, and a related substituted ligand-metal complex and catalyst, from the unsubstituted or substituted cyclopentene and unsubstituted or substituted acrylic acid. Also, the cyclic organic compound, ligand, and substituted ligand-metal complex and catalyst synthesized thereby. Also a method of polymerizing an olefin with the catalyst to give a polyolefin, and the polyolefin made thereby.

DETAILED DESCRIPTION

The Summary and Abstract are incorporated here by reference.

Certain inventive embodiments are described below as numbered aspects for easy cross-referencing. Additional embodiments are described elsewhere herein.

Aspect 1. A method of synthesizing a bicyclo[3.3.0] octene compound, the method comprising (A) contacting a compound of formula (1) ("compound (1)"):

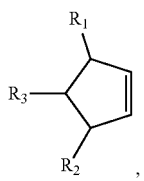

(1)

wherein R1, R2, and R3 are independently H or ($C_1$-$C_4$) alkyl, or R1 and R3 are bonded together to form a ($C_1$-$C_4$) alkylene and R2 is H or ($C_1$-$C_4$)alkyl, with a compound of formula (2) ("compound (2)"):

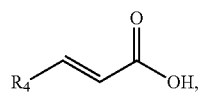

(2)

wherein R4 is H or ($C_1$-$C_4$)alkyl, in the presence of an effective amount of a phosphoric and/or sulfonic acid reagent and under reaction conditions sufficient to make a compound of formula (3) ("compound (3)"):

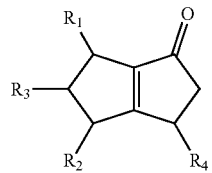

(3)

and/or its oxo/R4 regioisomer; wherein R1 to R4 are as defined above. The "/" in "oxo/R4 regioisomer" indicates the groups that are in different positions in the oxo/R4 regioisomer relative to the compound (3). That is, the positions of the oxo (=O) and R4 substituents are switched with each other relative to their positions in the compound (3). Thus, in the oxo/R4 regioisomer the oxo is bonded to the carbon atom bearing R4 in compound (3) and the R4 in the oxo/R4 regioisomer is bonded to the carbon atom bearing the oxo in compound (3). Functional groups that are in different positions in other regioisomers described below may be designated using "group/group" (e.g., R5/R4) in a similar manner. In some aspects when each of R1 to R3 is H and R4 is methyl, the phosphoric and/or sulfonic acid reagent and contacting step (A) are free of a polyphosphoric acid (PPA). In some aspects, the phosphoric and/or sulfonic acid reagent and contacting step (A) are free of PPA.

Aspect 2. A method of synthesizing a ligand for a transition metal, the method comprising: (A) synthesizing the compound (3):

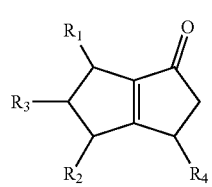

(3)

and/or its oxo/R4 regioisomer, according to step (A) of aspect 1, wherein R1 to R4 are as defined above (in aspect 1); (B) contacting the compound (3) and/or its oxo/R4 regioisomer with either a hydride-functional reducing agent or a ($C_1$-$C_4$)alkyl lithium, under reaction conditions sufficient to make a compound of formula (4) ("compound (4)"):

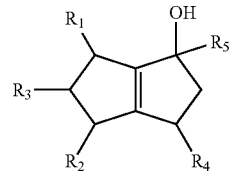

(4)

and/or its (HO,R5)/R4 regioisomer, respectively, wherein R1 to R4 are as defined above and R5 is either H or ($C_1$-$C_4$)alkyl, respectively; and (C) contacting the compound (4) and/or its (HO,R5)/R4 regioisomer with dehydration reaction conditions to make a compound of formula (5) ("compound (5)"):

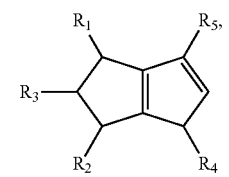

(5)

and/or its R5/R4 regioisomer, respectively, wherein the dehydration reaction conditions include temperature and a reagent effective for enhancing rate of loss of water from compound (4) and/or its (HO,R5)/R4 regioisomer; wherein R1 to R5 are as defined above. The "/" identifies the groups that are in different positions in the respective regioisomers relative to compound (4) or (5). In some aspects the method further comprises a separation step between steps (A) and (B), the separation step comprising separating the compound (3) from its oxo/R4 regioisomer to give a purified compound (3) and/or a purified oxo/R4 regioisomer. Alternatively, in some aspects the method further comprises a separation step between steps (B) and (C), the separation step comprising separating the compound (4) from its (HO,R5)/R4 regioisomer to give a purified compound (4) and/or a purified (HO,R5)/R4 regioisomer. Alternatively, in some aspects the method further comprises a separation step after step (C), the separation step comprising separating the compound (5) from its R5/R4 regioisomer to give a purified compound (5) and/or a purified R5/R4 regioisomer. Method steps downstream from one of the separation steps may be free of either the separated compound or its regioisomer, as the case may be and ultimately make the compound (5) that is free of its R5/R4 regioisomer or make the R5/R4 regioisomer that is free of the compound (5). The separation steps may comprise fractional distillation, fractional crystallization, or chromatography such as gas chromatography or liquid chromatography. E.g., room pressure, medium pressure or high pressure liquid chromatography on a silica gel column using one or more organic solvents as eluent.

Aspect 3. A method of synthesizing a zirconocene dichloride complex, the method comprising synthesizing the compound (5) and/or its R5/R4 regioisomer according to steps (A) to (C) of aspect 2; (D) contacting the compound (5) and/or its R5/R4 regioisomer with an alkyl lithium under reaction conditions sufficient to make a compound of formula (6) ("compound (6)"):

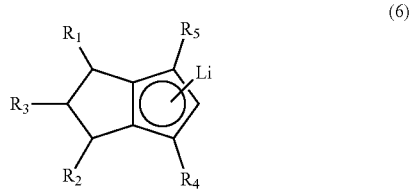

and/or its R5/R4 regioisomer, wherein R1 to R5 are as defined in aspect 2; and (E) contacting the compound (6) and/or its R5/R4 regioisomer with a compound of formula (7) ("compound (7)"):

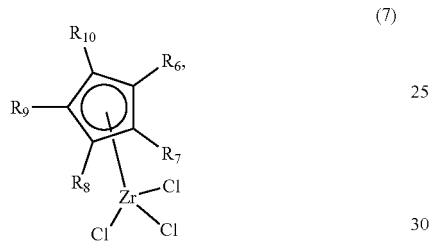

wherein R6 to R8 independently are H or $(C_1-C_4)$alkyl and R9 and R10 independently are H, $(C_1-C_4)$alkyl, or R9 and R10 are bonded together and are a $(C_3-C_5)$alkylene, under reaction conditions sufficient to make a compound of formula (8) ("compound (8)"):

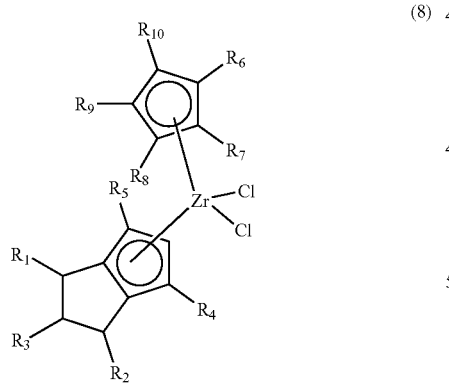

and/or its R5/R4 regioisomer, wherein R1 to R10 are as defined above. Method steps downstream from one of the separation steps described previously may be free of either the separated compound or its regioisomer, as the case may be and ultimately make the compound (8) that is free of its R5/R4 regioisomer or make the R5/R4 regioisomer that is free of the compound (8). The compound (7) may be made by contacting a R6 to R10-functional cyclopentadiene with an alkyl lithium under reaction conditions sufficient to make a R6 to R10-functional cyclopentadienyl lithium, and contacting the R6 to R10-functional cyclopentadienyl lithium with zirconium tetrachloride under reaction conditions sufficient to make the compound (7), wherein R6 to R10 are as defined above. The R6 to R10-functional cyclopentadiene may be synthesized by known methods or obtained from a commercial source. In some aspects R6 to R10 are H. In some aspects R6 is methyl and R7 to R10 are H. In some aspects R6 to R8 are H and R9 and R10 are bonded together and are a $(C_3-C_5)$alkylene. In some aspects the $(C_3-C_5)$alkylene is a 1,3-propane-diyl; alternatively a 1,4-butanediyl; alternatively a 1,5-pentanediyl. The compounds (7) and (8) wherein R9 and R10 are bonded together and are a $(C_3-C_5)$alkylene may be made by the inventive method starting from cyclopentene for R9 and R10 together being 1,3-propane-diyl; cyclohexene for R9 and R10 together being 1,4-butanediyl; or cycloheptene for R9 and R10 together being 1,5-pentanediyl. Alternatively, the compounds (7) and (8) wherein R9 and R10 are bonded together and are a $(C_3-C_5)$alkylene may be made by a conventional synthetic route. In some aspects compound (8) is of formula (8a):

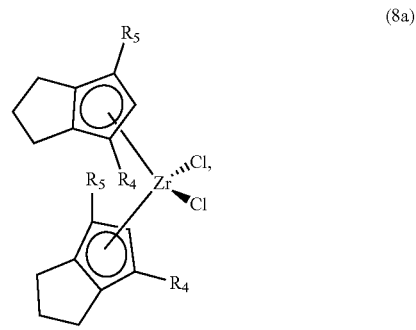

wherein R4 and R5 are independently as H or $(C_1-C_4)$alkyl.

Aspect 4. A method of synthesizing a zirconocene dimethyl complex, the method comprising synthesizing the compound (8) and/or its R5/R4 regioisomer according to steps (A) to (E) of aspect 3; and (F) contacting the compound (8) and/or its R5/R4 regioisomer with an effective amount of methyl magnesium bromide under reaction conditions sufficient to make a compound of formula (9) ("compound (9)"):

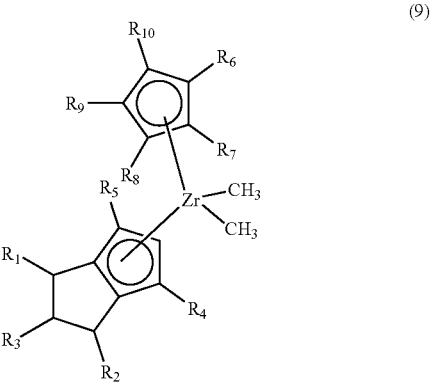

and/or its R5/R4 regioisomer, wherein R1 to R10 are as defined above (in aspect 3). Method steps downstream from one of the separation steps described previously may be free of either the separated compound or its regioisomer, as the case may be and ultimately make the compound (9) that is free of its R5/R4 regioisomer or make the R5/R4 regioisomer that is free of the compound (9). In some aspects R6 to R10 are H. In some aspects R6 is methyl and R7 to R10 are H. In some aspects R6 to R8 are H and R9 and R10 are bonded together and are a $(C_3-C_5)$alkylene. In some aspects the $(C_3-C_5)$alkylene is a 1,3-propane-diyl; alternatively a 1,4-butanediyl; alternatively a 1,5-pentanediyl. The compound (9) wherein R9 and R10 are bonded together and are a $(C_3-C_5)$alkylene may be made by the inventive method, alternatively by a conventional synthetic route. In some aspects compound (9) is of formula (8a) as defined above except wherein each Cl is replaced by methyl.

Aspect 5. The method of any one of aspects 1 to 4, wherein the phosphoric and/or sulfonic acid reagent is a polyphosphoric acid (PPA); a mixture of a phosphorous pentoxide and methanesulfonic acid ("$P_2O_5/H_3CSO_3H$ mixture"), or a reaction product thereof; or a combination of a PPA and a $P_2O_5/H_3CSO_3H$ mixture, or a reaction product of thereof.

Aspect 6. The method of any one of aspects 1 to 5 wherein the phosphoric and/or sulfonic acid reagent is a polyphosphoric acid (PPA).

Aspect 7. The method of any one of aspects 1 to 5, wherein the phosphoric and/or sulfonic acid reagent is, or consists essentially of, the $P_2O_5/H_3CSO_3H$ mixture, or a reaction product thereof. Alternatively the phosphoric and/or sulfonic acid reagent may consist essentially of an alkylsulfonic acid such as a $(C_1-C_6)$alkylsulfonic acid such as methanesulfonic acid. The expression "consist essentially of" means the phosphoric and/or sulfonic acid reagent and step (A) are free of PPA. In some aspects the $P_2O_5/H_3CSO_3H$ mixture is a 0.1/1 (weight/weight) $P_2O_5/H_3CSO_3H$ mixture, known as Eaton's reagent.

Aspect 8. The method of any one of aspects 1 to 5, wherein the phosphoric and/or sulfonic acid reagent is the combination of the PPA and the $P_2O_5/H_3CSO_3H$ mixture, or a reaction product thereof. In some aspects the $P_2O_5/H_3CSO_3H$ mixture is a 0.1/1 (weight/weight) $P_2O_5/H_3CSO_3H$ mixture, known as Eaton's reagent.

Aspect 9. The method of any one of aspects 1 to 8, characterized by any one of limitations (i) to (ix): (i) wherein at least one of R1 to R3 is a $(C_1-C_4)$alkyl or R4 is H; (ii) wherein each of R1 to R4 is H; (iii) wherein each of R1 to R3 is H and R4 is methyl; (iv) wherein in compound (1) each of R2 and R3 is H and R1 is methyl; in compound (2) R4 is methyl; and in compound (3) each of R2 and R3 is H and each of R1 and R4 is methyl; and in its oxo/R4 regioisomer each of R1 and R3 is H and each of R2 and R4 is each methyl; (v) wherein R1 and/or R2 is methyl and R3 is H; (vi) wherein R1 is methyl, R2 is 1-methylethyl (i.e., isopropyl), and R3 is H; (vii) wherein R1 is 1-methylethyl (i.e., isopropyl), R2 is methyl, and R3 is H; (viii) wherein R1 and R2 independently are $(C_1-C_4)$alkyl, R3 is H, and the stereochemistry of the carbon atom bonded to R1 is (R) and the stereochemistry to the carbon atom bonded to R2 is (S); and (ix) wherein R1 and R2 independently are $(C_1-C_4)$alkyl, R3 is H, and the stereochemistry of the carbon atom bonded to R1 is (S) and the stereochemistry to the carbon atom bonded to R2 is (R). Alternatively any one of limitations (x) to (xxiii): (x) both (vi) and (viii); (xi) both (vi) and (ix); (xii) both (vii) and (viii); (xiii) both (vii) and (ix); (xiv) wherein R5 is H; (xv) wherein R5 is methyl; (xvi) both (i) and (xiv) or (xv); (xvii) both (ii) and (xiv) or (xv); (xviii) both (iii) and (xiv) or (xv); (xix) both (iv) and (xiv) or (xv); (xx) both (v) and (xiv) or (xv); (xxi) wherein R9 and R10 are bonded together and are a $(C_3-C_5)$alkylene; (xxii) both (xxi) and any one of (i) to (xx); and (xxiii) R1 and R3 are bonded together to form a $(C_1-C_4)$alkylene and R2 is H or $(C_1-C_4)$alkyl.

Aspect 10. The compound (3) or its oxo/R4 regioisomer made by the method of aspect 1, the compound (4) or its (HO,R5)/R4 regioisomer made by the method of aspect 2, the compound (5) or its R5/R4 regioisomer made by the method of aspect 2, the compound (6) or (8), or their respective R5/R4 regioisomer made by the method of aspect 3, or the compound (9) or its R5/R4 regioisomer made by the method of aspect 4; wherein the compound or its regioisomer is free of platinum, palladium, nickel, rhodium, and ruthenium. The term "free of" means contains no detectable presence of. In some aspects the compound is any one of compounds (8-1), (8-2), (8-3), (8-4), (8a), and (8a-1); alternatively compound (9-1); described later in the Examples.

Aspect 11. A method of polymerizing an olefin, the method comprising contacting ethylene and/or an alpha-olefin with a catalyst made by contacting the compound (8) or (9), or its R5/R4 regioisomer, made by the method of aspect 4, with an activator, under conditions sufficient to make a polyolefin polymer comprising a polyethylene homopolymer, an ethylene/alpha-olefin copolymer, or a poly(alpha-olefin) homopolymer. In some aspects the catalyst is made from compound (8); alternatively from any one of compounds (8-1), (8-2), (8-3), (8-4), (8a), and (8a-1) described later in the Examples; alternatively from compound (9); alternatively from compound (9-1); described later in the Examples.

Aspect 12. The polyolefin polymer made by the method of aspect 11 and being free of platinum, palladium, nickel, rhodium, and ruthenium. In some aspects the polyolefin polymer is characterized by a butyl branch frequency (BBF) of 0.5 to less than 1.5, alternatively 0.6 to less than 1.2, alternatively 0.6 to less than 1.0, measured according to the Butyl Branch Frequency (BBF) Test Method, described later.

In another embodiment of any one of the foregoing aspects, except wherein 3,3-dimethyl-1-cyclopentene is used in place of the compound (1). The 3,3-dimethyl-1-cyclopentene is a geminal-dimethyl analog of cyclopentene and is a derivative of compound (1) wherein R2 and R3 are H, R1 is methyl, and the carbon atom bearing R1 is substituted with a second methyl. The embodiments yield analogs of compounds (3) to (6), (8) and (9) wherein R2 and R3 are H, R1 is methyl, and the carbon atom bearing R1 is substituted with a second methyl.

Compound: a molecule or a collection of same molecules.

Contacting: physically touching. In synthesizing context, contacting may be facilitated by a solvent that dissolves the compounds or materials being contacted.

Copolymer: macromolecular compound containing, in the same molecular entity or molecule, constitutional units derived from polymerizing a monomer and units derived from polymerizing at least one different monomer (comonomer).

Free of a polyphosphoric acid: no added polyphosphoric acid (PPA), alternatively no added, or in situ generated, PPA.

Homopolymer: macromolecular compound containing, in the same molecular entity or molecule, constitutional units, each of which is derived from polymerizing the same monomer.

Independently: without regard to or dependence on another.

Mixture: intimate blend of two or more compounds or materials.

Oxo: =O. E.g., as bonded to carbon atom in a carbonyl group (C=O).

Reaction product: different molecular entity than that from which it is made via a chemical reaction. The difference may be oxidation state and/or covalent bond(s).

Reagent, in the context of a reaction (e.g., step (A)): compound or mixture added to a reaction system to cause or enhance a desired chemical reaction.

Regioisomer: a positional isomer without any differences in bond multiplicities.

"$R_\#$" and "R #", wherein # means number, mean the same. E.g., $R_1$ and R1 are the same and mean a first R group; $R_2$ and R2 are the same and mean a second R group; and so on.

Step, in the context of the method of synthesizing: distinct chemical reaction, often with distinct reaction conditions and/or physical manipulations.

Stereochemistry: isomerism due to differences in spatial arrangement of atoms without any differences in connectivity or bond multiplicities between isomers.

Synthesizing: purposeful execution of one or more distinct chemical reactions or steps to manufacture a reaction product.

Zirconocene: complex comprising a zirconium atom bonded to one or two unsubstituted or substituted cyclopentadienyl-type groups, and optionally other ligands (e.g., $CH_3$, Cl).

Activator (for activating compound (9) and/or its R5/R4 regioisomer to form a catalyst). Also known as co-catalyst. Any metal containing compound, material or combination of compounds and/or substances, whether unsupported or supported on a support material, that can activate compound (9) and/or its R5/R4 regioisomer to give a catalyst and an activator species. The activating may comprise, for example, abstracting at least one leaving group (e.g., at least one methyl) from the Zr of compound (9) or its R5/R4 regioisomer to give the catalyst. The activator may be a Lewis acid, a non-coordinating ionic activator, or an ionizing activator, or a Lewis base, an alkylaluminum, or an alkylaluminoxane. The alkylaluminum may be a trialkylaluminum, alkylaluminum halide, or alkylaluminum alkoxide (diethylaluminum ethoxide). The trialkylaluminum may be trimethylaluminum, triethylaluminum ("TEAl"), tripropylaluminum, triisobutylaluminum, and the like. The alkylaluminum halide may be diethylaluminum chloride. The alkylaluminoxane may be a methyl aluminoxane (MAO), ethyl aluminoxane, or isobutylaluminoxane. The activator may be a MAO that is a modified methylaluminoxane (MMAO). The corresponding activator species may be a derivative of the Lewis acid, non-coordinating ionic activator, ionizing activator, Lewis base, alkylaluminum, or alkylaluminoxane, respectively. The activator species may have a different structure or composition than the activator from which it is derived and may be a by-product of the activation reaction. The metal of the activator typically is different than zirconium. The molar ratio of metal content of the activator to zirconium content of compound (9) and/or its R5/R4 regioisomer may be from 1000:1 to 0.5:1, alternatively 300:1 to 1:1, alternatively 150:1 to 1:1.

Alkyl means an unsubstituted univalent saturated acyclic hydrocarbon that is straight chain (1 or more carbon atoms), branched chain (if 3 or more carbon atoms), or cyclic (if 3 or more carbon atoms). Each $(C_1-C_4)$alkyl is independently methyl, ethyl, propyl, 1-methylethyl, butyl, 1-methylpropyl, 2-methylpropyl, or 1,1-dimethylethyl. Alternatively each $(C_1-C_4)$alkyl is independently a $(C_1-C_3)$alkyl; alternatively a $(C_2-C_4)$alkyl; alternatively $(C_1-C_2)$alkyl; alternatively $(C_2-C_3)$alkyl; alternatively $(C_3-C_4)$alkyl; alternatively methyl or $(C_3)$alkyl. In some aspects each $(C_1-C_4)$alkyl is independently a $(C_1-C_3)$alkyl and each $(C_1-C_3)$alkyl is independently methyl, ethyl, propyl, or 1-methylethyl; alternatively methyl, propyl, or 1-methylethyl; alternatively methyl; alternatively ethyl; alternatively propyl; alternatively 1-methylethyl. Substituted alkyl is an alkyl as defined above except wherein one or more hydrogen atoms is formally replaced by a substituent such as unsubstituted alkyl, halogen, or alkylcarboxylic ester.

Alkyl lithium is a compound of formula alkyl-Li. Examples of alkyl lithium are methyl lithium, ethyl lithium, propyl lithium, n-butyl lithium, sec-butyl lithium, t-butyl lithium, and pentyl lithium. The $(C_1-C_4)$alkyl lithium is an alkyl lithium wherein the alkyl is methyl, ethyl, propyl, 1-methyl ethyl, butyl, 1-methylpropyl, 2-methylpropyl (sec-butyl), or 1,1-dimethylethyl (t-butyl).

Alkylene is unsubstituted divalent saturated acyclic hydrocarbon that is straight chain (1 or more carbon atoms), branched chain (if 3 or more carbon atoms), or cyclic (if 3 or more carbon atoms). Each $(C_1-C_4)$alkylene is independently methylene ($CH_2$), ethylene ($CH_2CH_2$), propylene ($CH_2CH_2CH_2$), 1-methylethylene ($CH(CH_3)CH_2$), butylene (($CH_2)_4$), 1-methylpropylene ($CH(CH_3)CH_2CH_2$), 2-methylpropylene ($CH_2CH(CH_3)CH_2$), or 1,1-dimethylethylene ($C(CH_3)_2CH_2$. Substituted alkylene is an alkylene as defined above except wherein one or more hydrogen atoms is formally replaced by a substituent such as unsubstituted alkyl, halogen, or alkylcarboxylic ester.

Bicyclo[3.3.0]octene compounds are molecules having a five-membered carbocyclic ring fused to a five-membered carbocyclic ring. One of the five-membered carbocyclic ring may contain a carbon-carbon double bond, which may be shared at the fusion point with the other five-membered carbocyclic ring. Examples are (3), its oxo/R4 regioisomer, (4), its (HO,R5)/R4 regioisomer, (5), its R5/R4 regioisomer, (6), its R5/R4 regioisomer, (8), its R5/R4 regioisomer, (9), and its R5/R4 regioisomer.

Combination of polyphosphoric acid (PPA) and a mixture of a phosphorous pentoxide and methanesulfonic acid ("$P_2O_5/H_3CSO_3H$ mixture") is a physical blend of PPA and a preformed $P_2O_5/H_3CSO_3H$ mixture or a physical blend of PPA, $P_2O_5$, and $H_3CSO_3H$. In some aspects the method further comprises limitation (i) or (ii): (i) a step of preforming the combination of PPA and $P_2O_5/H_3CSO_3H$ mixture before the contacting step (A) and in the absence of at least one, alternatively each of the compounds (1) to (3) and the oxo/R4 regioisomer; or (ii) wherein the contacting step (A) further comprises contacting PPA and the $P_2O_5/H_3CSO_3H$ mixture together in the presence of at least one, alternatively each of the compounds (1) and (2) to form the combination of PPA and $P_2O_5/H_3CSO_3H$ mixture in situ.

Compound means a molecule or collection of molecules. When R1 to R3 is H, compound (1) is cyclopentene. When at least one of R1 to R3 is $(C_1-C_4)$alkyl, compound (1) is a substituted cyclopentene. When R4 is H, the compound (2) has CAS number 79-10-7 and is known as acrylic acid. When R4 is methyl, the compound (2) has CAS number 107-93-7 and is known as (E)-2-butenoic acid, crotonic acid, or (trans) 3-methylacrylic acid. Compounds (1) and (2) are widely available from commercial suppliers.

Dehydration reaction conditions include temperature and reagents effective for enhancing rate of loss of water from compound (4) and/or its (HO,R5)/R4 regioisomer. Example of such reagents are 1 Molar (M) or higher hydrochloric acid (aqueous HCl) or anhydrous HCl or Amberlyst 15 solid acid catalyst in an organic solvent such as ethanol, tetrahydrofuran or toluene. The hydrochloric acid may be from 1 M to 8 M, alternatively from 2 M to 6 M.

Effective amount is a quantity sufficient for enabling the making of a detectable amount of intended product. An effective amount of the phosphoric and/or sulfonic acid reagent is a quantity thereof sufficient for enabling the making of a detectable amount of compound (3) and/or its oxo/R4 regioisomer. Detectable amounts may be detected, and optionally characterized, by any suitable analytical method such as 1H-nuclear magnetic resonance (1H-NMR), high performance liquid chromatography (HPLC, versus a known standard), gas chromatography (GC, versus a known standard), or mass spectrometry; typically 1H-NMR. The effective amount of the phosphoric and/or sulfonic acid reagent used in step (A) may vary depending upon its composition, reaction conditions, and costs. A skilled person may determine an optimal effective amount thereof by starting with an initial reaction mixture of (1), (2), and 95 wt % of the phosphoric and/or sulfonic acid reagent, and thereafter systematically try reaction mixtures containing lower wt % of the phosphoric and/or sulfonic acid reagent until an optimal result under the reaction conditions is found. When the phosphoric and/or sulfonic acid reagent is PPA, the $P_2O_5/H_3CSO_3H$ mixture, or the combination of PPA and $P_2O_5/H_3CSO_3H$ mixture, the effective amount may be from 50 to 95 wt %, alternatively from 50 to 80 wt % based on total weight of (1), (2), and the phosphoric and/or sulfonic acid reagent. Alternatively, the effective amount of the $P_2O_5/H_3CSO_3H$ mixture may be from 1 to 10 mole equivalents, alternatively 1 to 5 mole equivalents, alternatively 1 to 3 mole equivalents thereof relative to the number of moles of compound (1). For example, if 1.0 mole of compound (1) is used in the contacting step (A), then the effective amount of the $P_2O_5/H_3CSO_3H$ mixture may be from 1 to 10 moles, alternatively from 1 to 5 moles, alternatively from 1 to 3 moles.

Hydride-functional reducing agent means a compound having a metal-H bond capable of adding to an oxo group of a ketone to give a tertiary alcohol. Suitable metals include Al and B. Suitable hydride-functional reducing agents are lithium aluminum hydride ($LiAlH_4$), diisobutyl aluminum hydride (i-$Bu_2AlH$), and sodium borohydride ($NaBH_4$).

Methanesulfonic acid is a compound of formula $H_3CSO_3H$ and has CAS number 75-75-2 and is widely available from commercial suppliers.

Mixture of a phosphorous pentoxide and methanesulfonic acid or $P_2O_5/H_3CSO_3H$ mixture is a blend or reaction product of phosphorous pentoxide and methane sulfonic acid. The weight/weight ratio of $P_2O_5/H_3CSO_3H$ in the mixture may be from 0.1 to 1 alternatively 0.15 to 1, alternatively 0.2 to 1. The 0.1/1 (wt/wt) $P_2O_5/H_3CSO_3H$ mixture is commercially available and may be referred to as Eaton's reagent. The mixture of $P_2O_5$ and $CH_3SO_3H$ may be formed in situ in the presence of the compound (1) and/or (2), such as prior to or during the contacting step (A). Alternatively, the mixture of $P_2O_5$ and $CH_3SO_3H$ may be preformed before contacting step (A). It is convenient to preform the $P_2O_5/CH_3SO_3H$ mixture before contacting step (A), and store the resulting preformed mixture for later use in embodiments of the contacting step (A). In some aspects the method further comprises limitation (i) or (ii): (i) a step of preforming the $P_2O_5/H_3CSO_3H$ mixture before the contacting step (A) and in the absence of at least one, alternatively each of the compounds (1) and (2); or (ii) wherein the contacting step further comprises contacting a phosphorous pentoxide and methanesulfonic acid together in the presence of at least one, alternatively each of the compounds (1) and (2) to form the $P_2O_5/H_3CSO_3H$ mixture in situ.

Phosphoric and/or sulfonic acid reagent is an acidic material having O-α(O)—OH acid groups and/or C—S(O)$_2$—OH acid groups, or an acidic reaction product thereof. The phosphoric and/or sulfonic acid reagent may be, or may consist essentially of, a mixture of a phosphorous pentoxide and methanesulfonic acid ("$P_2O_5/H_3CSO_3H$ mixture"), or a reaction product thereof; alternatively a polyphosphoric acid (PPA); alternatively a combination of a $P_2O_5/H_3CSO_3H$ mixture and a PPA, or a reaction product thereof. In some embodiments the phosphoric and/or sulfonic acid reagent consists essentially of the $P_2O_5/H_3CSO_3H$ mixture. Alternatively the phosphoric and/or sulfonic acid reagent may consist essentially of an alkylsulfonic acid such as a ($C_1$-$C_6$)alkylsulfonic acid such as methanesulfonic acid. The expression "consist essentially of" means the phosphoric and/or sulfonic acid reagent and step (A) are free of PPA.

Polyphosphoric acid or PPA has CAS no. 8017-16-1 and is a compound generally of formula HO—[P(=O)(OH)]$_n$—H, wherein subscript n indicates degree of polymerization. PPAs are widely available from commercial suppliers.

Phosphorous pentoxide is a compound of formula $P_2O_5$ and has CAS number 1314-56-3 and is widely available from commercial suppliers.

In some aspects each reactant, reagent, solvent, or other material used in the inventive methods, and each product thereof, is free of Pt, Ni, Pd, Rh, and Ru.

The "reaction conditions sufficient to make" mean appropriate for the desired chemical transformation, as is well understood in the art, and include reaction temperature; reaction pressure; reaction atmosphere; reaction solvent, if any; reactant and reagent concentrations; molar ratios of reactants to each other and to reagents; and absence of negating compounds. Reaction pressure is typically room pressure (e.g., 101 kilopascals (kPa), except higher for olefin polymerization reactions. If desired reactions (e.g., steps (A) to (F)) may be carried out in a fume hood under an anhydrous molecular nitrogen gas atmosphere or using Schlenck line techniques and conditions.

Reaction temperatures under reaction conditions sufficient to make may vary from step to step. For example, in step (A) (cyclocondensation) when the phosphoric and/or sulfonic acid reagent is PPA, the under reaction conditions sufficient to make compound (3) and/or its oxo/R4 regioisomer may include a reaction temperature of at least 40° C., alternatively at least 50° C., alternatively at least 65° C.; and at most 100° C., alternatively at most 95° C., alternatively at most 90° C., alternatively at most 80° C. In step (A) when using the $P_2O_5/H_3CSO_3H$ mixture the reaction temperature may be from −78° to 30° C., alternatively from −30° to 25° C., alternatively from 0° to 25° C. In steps (B) (hydride reduction or alkyl lithium addition), (D) (deprotonation of a cyclopentadiene), (E) (forming a zirconocene dichloride) and (F) (forming a zirconocene dimethyl) the reaction temperatures may be independently from −30° to 110° C., alternatively from 0° to 50° C., alternatively from 10° to 30° C. In step (C) (dehydration) the reaction temperature may be from 0° to 120° C., alternatively from 20° to 110° C., alternatively from 30° to 100° C.

The use or not of solvent and the type of solvent if used under reaction conditions sufficient to make may vary from step to step. Step (A) may be free of solvent or may employ a solvent. When the phosphoric and/or sulfonic acid reagent is PPA, a solvent may be omitted. When the phosphoric and/or sulfonic acid reagent is the $P_2O_5/H_3CSO_3H$ mixture, a polar aprotic solvent may be employed. The polar aprotic solvent may be selected from sulfolane, 1,2-dimethoxyethane, 1-methoxy-2-(2-methoxyethoxy)ethane, and mixtures of any two or more thereof. The amount of polar aprotic solvent employed is not particularly important. The foregoing polar aprotic solvents may serve to solubilize the compounds (1) and (2) and/or the $P_2O_5/H_3CSO_3H$ mixture. The amount of solvent employed may be sufficient to prepare a starting solution of that is from 0.5 Molar (M) to 5 M, or 1 M to 2.5 M of $P_2O_5/H_3CSO_3H$ mixture in the compound (2). The polar aprotic solvent may allow the contacting step (A) to be performed at lower temperatures within the ranges given above therefor. A polar aprotic solvent is used for the $P_2O_5/H_3CSO_3H$ mixture because a protic solvent is expected to undesirably react with the $P_2O_5/H_3CSO_3H$ mixture, which is a powerful dehydrating agent. The polar aprotic solvent may be of intermediate polarity in order to co-solubilize the compounds (1) and (2) and $P_2O_5/H_3CSO_3H$ mixture. The polar aprotic solvent may be capable of producing a homogeneous solution of the compounds (1) and (2) at 25° C., alternatively at 10° C., alternatively at 0° C. A homogeneous solution is not required for successful reaction of compounds (1) and (2) in the presence of the phosphoric and/or sulfonic acid reagent. In steps (B) (hydride reduction or alkyl lithium addition), (D) (deprotonation of a cyclopentadiene), (E) (forming a zirconocene dichloride) and (F) (forming a zirconocene dimethyl) an anhydrous, non-polar aprotic solvent such as an alkyl ether such as diethyl ether, tetrahydrofuran, or dioxane may be used. In step (B) when the hydride-functional reducing agent is used and is lithium aluminum hydride or diisobutyl aluminum hydride, the anhydrous, non-polar solvent is used. In step (B) when the hydride-functional reducing agent is used and is sodium borohydride, a polar protic solvent may be used such as methanol, ethanol, 2-propanol, or 1-methoxy-2-(2-methoxyethoxy)ethane. The alkyl lithium reagent may be dissolved in anhydrous alkane solvent such as hexanes, hexane, or heptane. Grignard reagents such as methyl magnesium bromide may be dissolved in an alkyl ether such as dialkyl ether.

Reaction atmosphere included under reaction conditions sufficient to make may be anhydrous molecular nitrogen gas or Schlenck line conditions for step (A) (cyclocondensation) and air for step (C) (dehydrating). Reaction atmosphere for step (B) (hydride reduction or alkyl lithium addition), (D) (deprotonation of a cyclopentadiene), (E) (forming a zirconocene dichloride) and (F) (forming a zirconocene dimethyl) may be an inert gas such as anhydrous nitrogen, argon or helium gas, or a mixture of any two or more thereof.

Reaction concentrations of reactants and reagents included under reaction conditions sufficient to make may be independently in the range from 0.1 to 1.4 M, alternatively 0.25 to 1 Molar (M), alternatively 0.4 to 1 M.

Molar ratios of reactants to each other and to reagents included under reaction conditions sufficient to make may vary from 0.25 times to 1.5 times theoretical reaction stoichiometry, alternatively from 0.99 times to 1.2 times theoretical reaction stoichiometry, alternatively from 1.0 to 1.1 times theoretical reaction stoichiometry, depending upon the reactants and reagents used. In step (A) (cyclocondensation) the theoretical reaction stoichiometry of compound (1) to compound (2) is 1.0 to 1.0. In step (B) (hydride reduction or alkyl lithium addition), the theoretical reaction stoichiometry of the hydride-functional reducing agent to compound (3) (or its regioisomer) is 0.25 LiAlH4 or NaBH4 to 1.0 compound (3) and 0.5 DIBAL-H to 1.0 compound (3) and 1.0 ($C_1$-$C_4$)alkyl lithium to 1.0 compound (3) (or its regioisomer). The theoretical reaction stoichiometry for step (C) (dehydration) is catalytic in acid catalyst up to, typically, 1:1. The theoretical reaction stoichiometry for each of steps (D) (deprotonation of a cyclopentadiene), or (E) (forming a zirconocene dichloride) is typically 1:1. The theoretical reaction stoichiometry for step (F) (forming a zirconocene dimethyl) is 2.0 methyl magnesium bromide to 1.0 compound (8) (or its R5/R4 regioisomer).

Negating agents should not be included under reaction conditions sufficient to make. In step (A) (cyclocondensation), a negating agent may be a quantify of a basic compound that would neutralize the acidity of the phosphoric and/or sulfonic acid reagent or otherwise render it ineffective; or a negating agent may be an unsaturated aliphatic compound that would react with compound (2) before compound (2) could react with compound (1). In steps (B) (hydride reduction or alkyl lithium addition), (D) (deprotonation of a cyclopentadiene), (E) (forming a zirconocene dichloride) and (F) (forming a zirconocene dimethyl), a negating agent would be a protic compound (e.g., a NH functional, OH functional, and/or SH functional compound) or a strong oxidizing agent. Examples of NH functional compounds are primary and secondary amines and amides. Examples of OH functional compounds are alcohols, carboxylic acids, and oximes. Examples of SH functional compounds are thiols (mercaptans). Examples of NH and OH functional compounds are primary and secondary amino alcohols and amino acids. In step (C) (dehydrating), a negating agent would be added water (not counting water formed as a by-product of the dehydrating step) or a quantity of a basic compound that would neutralize an acid dehydration catalyst used therein.

A compound includes all its isotopes and natural abundance and isotopically-enriched forms. The enriched forms may have medical or anti-counterfeiting uses.

In some aspects any compound, composition, formulation, mixture, or reaction product herein may be free of any one of the chemical elements selected from the group consisting of: H, Li, Be, B, C, N, O, F, Na, Mg, Al, Si, P, S, Cl, K, Ca, Sc, Ti, V, Cr, Mn, Fe, Co, Ni, Cu, Zn, Ga, Ge, As, Se, Br, Rb, Sr, Y, Zr, Nb, Mo, Tc, Ru, Rh, Pd, Ag, Cd, In, Sn, Sb, Te, I, Cs, Ba, Hf, Ta, W, Re, Os, Ir, Pt, Au, Hg, Tl, Pb, Bi, lanthanoids, and actinoids; with the proviso that chemical elements required by the compound, composition, formulation, mixture, or reaction product (e.g., C and H required by a polyolefin or C, H, and O required by an alcohol) are not excluded.

The following apply unless indicated otherwise. Alternatively precedes a distinct embodiment. ASTM means the standards organization, ASTM International, West Conshohocken, Pa., USA. Any comparative example is used for illustration purposes only and shall not be prior art. Free of or lacks means a complete absence of; alternatively not detectable. May confers a permitted choice, not an imperative. Operative means functionally capable or effective. Optional(ly) means is absent (or excluded), alternatively is present (or included). Properties are measured using a standard test method and conditions for the measuring (e.g., viscosity: 23° C. and 101.3 kPa). Ranges include endpoints, subranges, and whole and/or fractional values subsumed therein, except a range of integers does not include fractional values. Room temperature: 23° C.±1° C. Substituted when referring to a compound means having, in place of hydrogen, one or more substituents, up to and including per substitution.

EXAMPLES

Unless noted otherwise herein, use the following preparations for characterizations. Carry out syntheses under an atmosphere of dry nitrogen in a glovebox when indicated. Perform reactions requiring anhydrous conditions under an atmosphere of dry nitrogen in oven-dried glassware cooled under a stream of dry nitrogen. Anhydrous toluene, hexanes, tetrahydrofuran, diethyl ether and 1,2-dimethoxyethane are from Sigma-Aldrich. Solvents that are used for experiments performed in a nitrogen-filled glovebox are further dried by storage over activated 4 Angstrom (A) molecular sieves. Cyclopentadienylzirconium (IV) chloride (compound (7) wherein R6-R10 is H, "(Cp)ZrCl$_3$") and zirconium (IV) chloride (ZrCl$_4$) complex with dimethoxyether (DME) are purchased from Boulder Scientific and is used as received. Methylcyclopentadienylzirconium (IV) chloride (compound (7) wherein R6-R9 is H and R10 is methyl, "(MeCp)ZrCl$_3$") is purchased as a complex with DME from Boulder Scientific and is used as received. Propylcyclopentadienylzirconium (IV) chloride (compound (7) wherein R6-R9 is H and R10 is propyl, "(PrCp)ZrCl$_3$") is purchased as a complex with DME from Boulder Scientific and is used as received. Tetramethylcyclopentadienylzirconium (IV) chloride (compound (7) wherein R6-R9 is methyl and R10 is H, "(Me$_4$Cp)ZrCl$_3$") is purchased from Boulder Scientific and is used as received. All other reagents are purchased from Sigma-Aldrich and are used as received. For example, P$_2$O$_5$/CH$_3$SO$_3$H (0.1/1 wt/wt) may be purchased from Sigma-Aldrich, CAS #39394-84-8.

$^1$H-NMR (proton nuclear magnetic resonance spectroscopy) chemical shift data are reported in parts per million (ppm) down field relative to tetramethylsilane (TMS), 6 scale, using residual protons in deuterated solvent as references. The $^1$H-NMR chemical shift data measured in CDCl$_3$ are referenced to 7.26 ppm, data measured in benzene-d6 (C$_6$D$_6$) to 7.16 ppm, data measured in tetrahydrofuran-d8 (THF-d8) to 3.58 ppm. $^1$H-NMR chemical shift data are reported in the format: chemical shift in ppm (multiplicity, coupling constant(s) in Hertz (Hz), and integration value. Multiplicities are abbreviated s (singlet), d (doublet), t (triplet), q (quartet), pent (pentet), m (multiplet), and br (broad).

GC/MS (EI) means gas chromatography-mass spectrometry (electron ionization).

Butyl Branch Frequency (BBF) Test Method: Butyl Branching Frequency is number of butyl branches per 1000 main chain carbon atoms of a poly(ethylene-co-1-hexene) copolymer. To prepare test sample, add approximately 2.74 g of a 50/50 mixture of tetrachloroethane-d2/orthodichlorobenzene containing 0.025 M Cr(AcAc)$_3$ to 0.15 g of test sample of the copolymer in a 10 mm NMR tube (Norell 1001-7). Remove oxygen manually by purging tube with nitrogen using a Pasteur pipette for 1 minute. Dissolve and homogenize test sample by heating the tube and its contents to 150° C. in a heating block. Visually inspect heated test sample to ensure homogeneity (thorough mixing). Without allowing heated test sample to cool, insert it into a heated (120° C.) NMR probe. Allow inserted sample to thermally equilibrate at the probe temperature for seven minutes. Then acquire NMR data using a Bruker 400 MHz spectrometer, equipped with a Bruker CryoProbe using 320 transient scans, and a six second pulse repetition delay. Make all measurements on a non-spinning sample in locked mode. Internally reference $^{13}$C NMR chemical shifts to the EEE triad at 30 ppm. Determine short chain branches (SCB) derived from 1-hexene (C4 branches) comonomeric units by setting the integral value for the entire spectrum (from ~40 to 10 ppm) to 1,000, and then calculate BBF according to the following formula: BBF=(a+b/2+c+d/2+e)/5, wherein a, b, c, d, e and f are the integrated regions of the $^{13}$C NMR signals at 38.2, 34.6, 34.2, 27.3 and 23.4 ppm, respectively.

Melt Temperature Test Method: melt temperature of a polymer is determined by Differential Scanning calorimetry according to ASTM D 3418-08. For instance, using a scan rate of 10° C./minute on a sample of 10 mg and using the second heating cycle.

Molecular Weights Test Method: determine molecular weights (MW) including weight-average molecular weight (Mw), number average molecular weight (Mn), and z-average molecular weight (Mz), and calculate molecular weight distribution (Mw/Mn or MWD) by using a High Temperature Gel Permeation Chromatography (Polymer Laboratories), equipped with a differential refractive index detector (DRI). Use three Polymer Laboratories PLgel 10 µm Mixed-B columns, nominal flow rate 1.0 milliliter per minute (mL/min.), and nominal injection volume 300 microliters (µL). House transfer lines, columns, and differential refractometer (the DRI detector) in an oven maintained at 160° C. Measure all quantities gravimetrically. Prepare solvent by dissolving 6 grams of butylated hydroxytoluene (antioxidant) in 4 liters of reagent grade 1,2,4-trichlorobenzene (TCB). Filter the TCB mixture through a 0.1 micrometer (µm) Teflon filter. Degas the filtrate with an in-line degasser before it enters the GPC instrument. Prepare test polymer solutions by placing test sample of dry polymer in glass vials, adding an amount of TCB sufficient to give an injection concentration from 0.5 to 2.0 mg/mL, using lower concentrations for higher molecular weight samples. Then heat the mixture at 160° C. with continuous shaking for 2 hours to give a ready test sample. Prior to running each ready test sample, purge the DRI detector. Before injecting each ready test sample, increase flow rate in the apparatus to 1.0 mL/min., and allow the DRI detector to stabilize for 8 hours. Determine molecular weights (MW) by combining universal calibration relationship with the column calibration, which is performed with a series of monodispersed polystyrene (PS) standards. Calculate MW at each elution volume with following equation:

$$\log M_X = \frac{\log(K_X/K_{PS})}{a_X+1} + \frac{a_{PS}+1}{a_X+1}\log M_{PS},$$

wherein subscript "X" indicates test sample and subscript "PS" indicates PS standard. In this method, $a_{PS}$=0.67 and $K_{PS}$=0.000175 and obtain $a_X$ and $K_X$ from published literature. Specifically, a/K=0.695/0.000579 for polyethylenes (PE) and 0.705/0.0002288 for polypropylenes (PP). Calculate concentration, c, at each point in the chromatogram from the baseline-subtracted DRI signal, $I_{DRI}$, using the following equation: c=$K_{DRI}I_{DRI}$/(dn/dc), where $K_{DRI}$ is a constant determined by calibrating the DRI, and (dn/dc) is the refractive index increment for the system. Specifically, do/dc=0.109 for polyethylene. Calculate mass recovery from the ratio of the integrated area of the concentration chromatography over elution volume and the injection mass, which is equal to the pre-determined concentration multiplied by injection loop volume. Report all molecular weights in g/mol unless otherwise noted. In event of conflict between the GPC-DRI procedure and the "Rapid GPC," the GPC-DRI procedure immediately above shall be used. If desired, see US 2006/0173123 A1, pages 24-25, paragraphs [0334] to [0341], for further details on determining Mw, Mn, Mz, MWD.

Inventive Example 1: synthesis of compound (3-1) (compound (3) wherein R1 to R3 is H and R4 is methyl) using $P_2O_5/H_3CSO_3H$ mixture: In a fume hood, under a nitrogen atmosphere in a 250 mL round bottom flask equipped with a stir bar, (E)-2-butenoic acid (compound (2) wherein R4 is methyl, 5 g, 57.5 millimoles (mmol)) is added followed by cyclopentene (compound (1) wherein R1 to R3 is H, 5.6 mL, 63.3 mmol). The reaction mixture is cooled to 0° C. Next, $P_2O_5/H_3CSO_3H$ mixture (0.1/1) is added dropwise (55.3 mL, 348 mmol) at 0° C. The reaction mixture, with stirring, is warmed up to room temperature and then stirring is continued for 20 hours. The resulting crude product is diluted with 50 mL of water. Solid $NaHCO_3$ is added until bubbling subsides. The reaction mixture reaches pH 8 to pH 9. The aqueous and organic layers are separated in a separatory funnel. The aqueous layer is extracted three times with diethyl ether (3×50 mL). The organic layers are combined and washed with brine (50 mL), dried over anhydrous magnesium sulfate and filtered. The solvent is removed in vacuo to afford 5.7 g of compound (3-1) as a dark brown liquid product (72% yield). Compound (3-1) was characterized by $^1$H-NMR and GC/MS (EI). $^1$H-NMR (400 MHz, $CDCl_3$) δ 2.87 (ddt, 1H), 2.83-2.72 (m, 1H), 2.56-2.44 (m, 1H), 2.41-2.17 (m, 6H), 1.10 (d, 3H).

Inventive Example 2: synthesis of compound (3-1) (compound (3) wherein R1 to R3 is H and R4 is methyl) using PPA:A 3-necked, 250 mL round bottom flask fitted with a mechanical stirrer and under a nitrogen atmosphere is charged with polyphosphoric acid (PPA) (66 g) and warmed up to 65° C. until the PPA becomes soluble. (E)-2-butenoic acid (compound (2) wherein R4 is methyl, also known as crotonic acid, 3.0 g, 34.8 mmol) is added, followed by the dropwise addition of cyclopentene (compound (1) wherein R1 to R3 is H, 3.08 mL, 34.8 mmol). The resulting reaction mixture turns bright orange. The reaction mixture is mechanically stirred at 65° C. for 1.5 hours. The resulting dark brown thick reaction mixture is poured onto ice/water. The mixture is extracted three times with diethyl ether (3×60 mL). The organic layers are combined with saturated aqueous sodium bicarbonate (100 mL), and stirred for 20 minutes until bubbling subsides. The organic layer is separated and is further washed with saturated bicarbonate (2×60 mL). The organic layer is washed with brine (60 mL), dried over anhydrous magnesium sulfate, and filtered. The solvent is removed in vacuo, the obtained product was refined by silica gel chromatography (diethyl ether/hexane) to afford 1.2 g of compound (3-1) as a light brown liquid (24% yield). $^1$H-NMR (400 MHz, $CDCl_3$) δ 2.93 (dd, 1H), 2.88-2.78 (m, 1H), 2.63-2.48 (m, 1H), 2.47-2.23 (m, 6H), 1.16 (d, 3H).

Inventive Example 3: synthesis of compound (4-1): compound (4) wherein R1 to R3 is H and R4 and R5 are methyl. Under an atmosphere of dry nitrogen, the compound (3-1) of Inventive Example 2 (1.1 g, 8.08 mmol) is weighed out in a 100 mL round bottom flask and is dissolved in anhydrous diethyl ether (17 mL). The reaction mixture is cooled to −78° C. Methyl lithium (1.6 M, 6.31 mL, 10.1 mmol) is added dropwise and the solution is stirred for 15 minutes at −78° C. The reaction mixture is stirred for 20 hours at room temperature to give a reaction mixture containing compound (4-1). Compound (4-1) was not isolated or characterized by $^1$H-NMR. It may be characterized by GC/MS (EI).

Inventive Example 4: synthesis of compound (5-1): compound (5) wherein R1 to R3 is H and R4 and R5 are methyl. To the reaction mixture containing compound (4-1) in Inventive Example 3 is added aqueous 6 M HCL (5.3 mL) and stirred for 20 hours at room temperature. The organic phase is separated and the aqueous layer is extracted with diethyl ether (2×25 mL). The combined organic layers are washed with water (50 mL), followed saturated $NaHCO_3$ (50 mL) and brine (50 mL). The organic layers are dried over magnesium sulfate and filtered, and the solvent is removed in vacuo. The obtained product was refined by passing it through a silica gel plug and eluting with diethyl ether/hexane to give 0.7 g of compound (5-1) in 65% overall yield from compound (3-1) of Inventive Example 2. Obtained as a mixture of double bond regioisomers. $^1$H-NMR (400 MHz, $CDCl_3$) δ 3.16-2.98 (m, 2H), 2.43-1.88 (series of multiplets, 13H).

Inventive Example 5: synthesis of compound (6-1): compound (6) wherein R1 to R3 is H and R4 and R5 are methyl. In a glove box, in a 120 mL glass jar, compound (5-1) (0.7 g, 5.22 mmol) is dissolved in hexanes (26 mL). To the stirred solution is added dropwise a solution of n-butyl lithium in hexanes (1.6 M, 3.92 mL, 6.27 mmol). The reaction mixture is stirred for 20 hours. The compound (6-1) is collected by vacuum filtration, and the resulting solid product is washed with hexanes and dried under vacuum to give 0.28 g of compound (6-1) in 38% yield. $^1$H-NMR (400 MHz, THF-$d_8$) δ 5.02 (s, 1H), 2.37 (m, 4H), 2.11 (m, 2H), 1.89 (s, 6H).

Inventive Example 6: synthesis of compound (8-1): compound (8) wherein R1 to R3 and R6 to R10 are H and R4 and R5 are methyl. In drybox in a 120 mL glass jar, (Cp)ZrCl$_3$ (compound (7) wherein R6 to R10 are H, 0.52 g, 1.97 mmol) is slurried in 9 mL of 1,2-dimethoxyethane and stirred. To the stirred reaction mixture is added compound (6-1) (0.28, 1.97 mmol) in small portions. The resulting reaction mixture is stirred for 48 hours at room temperature. The resulting reaction mixture was evaporated in vacuo to remove the solvent. The resulting solid was extracted with dichloromethane and filtered to give 0.21 g of compound (8-1) in 30% yield. $^1$H-NMR (400 MHz, Benzene-$d_6$) δ 6.01 (s, 5H), 5.34 (s, 1H), 2.94 (m, J=2H), 2.34-2.16 (m, 3H), 2.05-1.87 (m, 1H), 1.66 (s, 6H).

Inventive Example 7 (prophetic): compound (9-1): compound (9) wherein R1 to R3 and R6 to R10 are H and R4 and R5 are methyl. In drybox in an 240 mL glass jar, compound (8-1) (10.5 mmol) is slurried in anhydrous diethyl ether (65 mL). To the stirred reaction mixture is added a solution of methyl magnesium bromide (3.0 M, 7.89 mL, 23.7 mmol) dropwise. The reaction mixture is stirred for 20 hours at room temperature. The solvent is removed under vacuum. The resulting solid product is dissolved in hexanes (150 mL) and filtered. The hexanes are removed under vacuum to afford compound (9-1).

Inventive Example 8 (prophetic): synthesis of compound (3-2) and its oxo/R4 regioisomer using $P_2O_5/H_3CSO_3H$ mixture: compound (3) wherein R1 and R2 is H and R3 and R4 are methyl, and its oxo/R4 regioisomer. In a fume hood under a nitrogen atmosphere, in a round bottom flask equipped with a stir bar, (E)-2-butenoic acid (compound (2) wherein R4 is methyl, 1 g, 11.6 mmol) is added followed by 4-methyl-1-cyclopentene (compound (1) wherein R3 is methyl, 11.6 mmol). Next, 1,2-dimethoxyethane is added (5.5 mL). The reaction mixture is cooled to −20° C. Next, add $P_2O_5/H_3CSO_3H$ mixture (0.1:1) dropwise (5.53 mL, 34.8 mmol) at −20° C. The reaction mixture, with stirring, is warmed up to room temperature and then stirring is continued for 20 hours. The mixture is diluted into 50 mL of water and 50 mL of diethyl ether. Solid $NaHCO_3$ is added until bubbling subsides. The liquid layer is decanted and the aqueous and organic layers are separated. The aqueous layer is extracted twice with diethyl ether (2×15 mL). The combined organic layers are combined and washed with saturated $NaHCO_3$ (20 mL). The organic layer is washed with brine (30 mL), dried over magnesium sulfate and filtered. The solvent is removed in vacuo to afford compound (3-2) and its oxo/R4 regioisomer.

Inventive Example 9 (prophetic): polymerization of ethylene using a catalyst prepared from compound (8-1) or (9-1). Use a gas-phase fluidized bed reactor ("Reactor") having a reaction zone dimensioned as 304.8 mm (twelve inch) internal diameter and a 2.4384 meter (8 feet) in straight-side height and containing a fluidized reactor bed of polymer granules. Configure the Reactor with a recycle gas line for flowing a recycle gas stream. Fit the Reactor with gas feed inlets and polymer product outlet. Introduce gaseous feed streams of ethylene and hydrogen together with liquid 1-hexene comonomer below the fluidized reactor bed into the recycle gas line. Control individual flow rates of ethylene ("C2"), hydrogen ("H2") and 1-hexene ("C6") to maintain a fixed 1-hexene comonomer to ethylene monomer composition molar ratio ("C6/C2") from 0.0001 to 0.1 (e.g., 0.0050), a constant hydrogen to ethylene molar ratio ("H2/C2") from 0.0001 to 0.1 (e.g., 0.0020), and a constant ethylene ("C2") partial pressure from 1,000 to 2,000 kilopascals (kPa) (e.g., 1,500 kPa). Measure concentrations of all gases by an in-line gas chromatograph to ensure relatively constant composition in the recycle gas stream. Maintain a reacting bed of growing polymer particles in a fluidized state by continuously flowing a make-up feed and recycle gas through the reaction zone. Use a superficial gas velocity of from 0.4 to 0.7 meter per second (m/sec) (e.g., from 0.49 to 0.67 m/sec, or 1.6 to 2.2 feet per second (ft/sec)). Operate the Reactor at a total pressure of 2,000 to 3,000 kPa (e.g., 2344 to about 2413 kPa, or 340 to about 350 pounds per square inch-gauge (psig)) and at a constant reaction temperature of 85° to 115° C. (e.g., 105° C.). Maintain the fluidized bed at a constant height by withdrawing a portion of the bed at a rate equal to the rate of formation of particulate product. The polymer production rate is in the range of 5 to 20 kg/hour (e.g., 13 to 18 kg/hour. Remove the polymer product semi-continuously via a series of valves into a fixed volume chamber, wherein this removed polymer product is purged to remove entrained hydrocarbons and treated with a stream of humidified nitrogen (N2) gas to deactivate any trace quantities of residual polymerization catalyst. A polyethylene is made and characterized by melt index 12 (190 C., 2.16 kg, ASTM D1238-13); density (ASTM D792-13, Method B); Butyl branching frequency* (BBF, NMR), wherein BBF is the number of butyl branches per 1000 main chain carbon atoms; number average molecular weight; weight average molecular weight; molecular mass dispersity ($M_w/M_n$), $Đ_M$ (pronounced D-stroke M), and melting temperature $T_m$.

Inventive Example 10: synthesis of compound (8-2): compound (8) wherein R1 to R3 and R6 to R9 are H and R10, R4, and R5 are methyl. In a drybox in a 120 milliliter (mL; 4-ounzes) glass jar, slurried the (MeCp)ZrCl$_3$-DME complex (0.88 g, 2.85 mmol) in 20 mL of toluene. Stirred the resulting mixture, and to it added compound (6-1) (0.5 g, 3.57 mmol) in small portions. Stirred the resulting reaction mixture for 48 hours at room temperature, filtered, and removed the solvent under vacuum from the filtrate to give a brown solid crude product. Triturated the crude product by slurrying it in 35 mL of pentane and stirring for 4 hours at room temperature. Filtered the triturated mixture to give 0.28 g purified solid compound (8-2) in 26% yield. $^1$H NMR (400 MHz, Benzene-d$_6$) δ 5.86 (t, J=2.7 Hz, 2H), 5.76 (t, J=2.7 Hz, 2H), 5.35 (s, 1H), 3.04-2.89 (m, 2H), 2.37-2.23 (m, 3H), 2.19 (s, 3H), 2.04-1.92 (m, 1H), 1.67 (s, 6H).

Inventive Example 11: synthesis of compound (8-3): compound (8) wherein R1 to R3 and R6 to R9 are H, R10 is propyl, and R4 and R5 are methyl. In drybox in a 120 mL glass jar, slurried the (PrCp)ZrCl$_3$-DME complex (1.13 g, 2.85 mmol) in 20 mL of toluene. Stirred the resulting mixture, and to it added compound (6-1) (0.5 g, 3.57 mmol) in small portions. Stirred the resulting reaction mixture for 48 hours at room temperature, filtered, and removed the solvent under vacuum from the filtrate to give a brown solid crude product. Triturated the crude product by slurrying it in pentane (20 mL), with stirring for 4 hours at room temperature. Filtered the triturated mixture, and triturated it with fresh pentane (20 mL) with stirring for 4 hours at room temperature. Filtered the second triturated mixture to give 0.28 g of purified solid compound (8-3) in 24% yield. $^1$H NMR (400 MHz, Benzene-d$_6$) δ 5.97-5.85 (m, 2H), 5.81-5.68 (m, 2H), 5.39 (s, 1H), 3.06-2.92 (m, 2H), 2.72-2.64 (m, 2H), 2.38-2.22 (m, 3H), 2.06-1.93 (m, 1H), 1.69 (s, 6H), 1.58-1.39 (m, 3H), 0.83 (t, J=7.4 Hz, 3H).

Inventive Example 12: synthesis of compound (8-4): compound (8) wherein R1 to R3 and R6 is H, and to R7 to R10 and R4 and R5 are methyl. Replicated Inventive Example 11 except used (Me$_4$Cp)ZrCl$_3$ (0.96 g, 2.85 mmol) instead of the (PrCp)ZrCl$_3$-DME complex to give 0.57 g purified solid compound (8-4) in 48% yield. $^1$H NMR (400 MHz, Benzene-d$_6$) δ 5.41 (s, 1H), 5.26 (s, 1H), 3.15-3.04 (m, 2H), 2.56-2.41 (m, 1H), 2.37 (dt, J=14.7, 8.5 Hz, 2H), 2.13-2.02 (m, 1H), 2.01 (s, 6H), 1.79 (s, 6H), 1.69 (s, 6H).

Inventive Example 13: synthesis of compound (8a-1): compound (8a) wherein R4 and R5 are methyl. In a drybox in a 240 mL glass jar, slurried ZrCl$_4$-DME complex (0.83 g, 3.56 mmol) in 20 mL of toluene and stirred. Added 0.99 g (7.12 mmol) of compound (6-1) in small portions, and stirred the resulting reaction mixture for 48 hours at room temperature. Filtered and removed solvent from filtrate under vacuum to give brown solid. Triturated twice, each by slurrying in 40 mL of pentane, stirring for 4 hours at room temperature, and filtering to give 0.34 g purified solid compound (8-4) in 22% yield. $^1$H NMR (400 MHz, Benzene-d$_6$) δ 5.40 (s, 2H), 3.09 (ddd, J=14.6, 8.6, 1.7 Hz, 4H), 2.61-2.44 (m, 2H), 2.38 (dt, J=14.5, 8.5 Hz, 4H), 2.12-1.98 (m, 2H), 1.75 (s, 12H).

Inventive Example 14: synthesis of compound (6-2): compound (6) wherein R1 to R3 is H, R4 is H and R5 is methyl via a sequence of reaction steps comprising (14a) reduction, (14b) dehydration, and (14c) deprotonation.

Inventive Example 14a: synthesis of compound (4-2): compound (4) wherein R1 to R3 is H, and R4 is H and R5 is methyl. Under an atmosphere of dry nitrogen, weighed the compound (3-1) of Inventive Example 2 (1.06 g, 7.78 mmol) in a 250 mL round bottom flask, and dissolved it in anhydrous diethyl ether (32 mL). In a separate 250 mL round bottom flask prepared a suspension of lithium aluminum hydride solution (1.0 M, 8.25 mL, 8.25 mmol) in anhydrous diethyl ether (20 mL), and cooled the suspension to 0° C. Added the solution in diethyl ether of compound (3-1) to the cooled lithium aluminum hydride suspension over 15 minutes, and stirred the resulting reaction mixture at 0° C. for 1 hour. Decomposed excess lithium aluminum hydride by addition of water (20 mL). Separated the resulting organic phase from the aqueous layer and the inorganic salts. Extracted the aqueous layer with dichloromethane (3×50 mL). Combined the ether and dichloromethane layers, and washed the combination with brine (50 mL), dried over magnesium sulfate and filtered. Removed solvent from the filtrate in vacuo to give 0.74 g of compound (4-2) in 69% yield. Compound (4-2) is characterized by GC/MS (EI) 138 (mass), 123, 95.

Inventive Example 14b: synthesis of compound (5-2): compound (5) wherein R1 to R3 is H, and R4 is H and R5 is methyl. Dissolved compound (4-2) (0.74 g, 5.35 mmol) in anhydrous diethyl ether (35 mL), and cooled solution to 0° C. Added Amberlyst 15 acid resin (1.3 g) to the solution, and stirred the resulting reaction mixture for 1 hour at 0° C., and warmed up to room temperature. Added magnesium sulfate and stirred the mixture for 10 minutes. Filtered the mixture, and removed solvent from the filtrate in vacuo to give 0.49 g of compound (5-2) as a mixture of isomers in 76% yield.

Inventive Example 14c: synthesis of compound (6-2): compound (6) wherein R1 to R3 is H, R4 is H, and R5 is methyl. In a glove box under anhydrous nitrogen atmosphere, dissolved compound (5-2) (0.49 g, 4.07 mmol) in pentane (20 mL) in a 250 mL round bottom flask. Cooled solution down to −35° C. for 20 minutes. To the stirred solution added dropwise a solution of n-butyl lithium in hexanes (1.6 M, 3.06 mL, 4.89 mmol). Stirred the resulting reaction mixture for 20 hours. Collected compound (6-2) by vacuum filtration, and washed the solid product with pentane, and dried under vacuum to give 0.12 g of compound (6-2) in 24% yield. $^1$H NMR (400 MHz, THF-$d_8$) δ 5.35-5.16 (m, 1H), 2.26-2.01 (m, 2H), 1.98 (s, 3H), 1.68-1.53 (m, 4H), 1.50-1.42 (m, 2H).

Inventive Examples 15 to 19: synthesis of spray-dried polymerization catalysts. In separate experiments, prepared a polymerization catalyst system using one of polymerization catalysts of Inventive Example 6, 10, 11, 12, and 13, respectively, as follows. Slurried 5.30 g of treated (hydrophobic) fumed silica (Cabosil TS-610) in 125 g of toluene. Then added 44 g of a 10 wt % solution of methylaluminoxane (MAO) in toluene. Next, added the polymerization catalyst of Inventive Example 6, 10, 11, 12, or 13, and stirred the resulting mixture for 30 to 60 minutes. Used a spray-drier apparatus configured with an inlet and outlet and an atomizing device, a heated spray drier, and a cyclone separator. Introduced the resulting mixture into the spray-drier via the inlet into the atomizing device, producing droplets that were then contacted with a hot nitrogen gas stream to evaporate the liquid and form a powder. Separated the powder from the gas mixture in the cyclone separator, and discharged the separated fine powder through the outlet into an external container. During the foregoing spray-drying procedure, the spray drier temperature was set at 165° C. and the outlet temperature at 60° to 70° C. All loadings of the catalyst of Inventive Examples 6, 10, 11, 12, or 13 were 50 micromoles of catalyst per gram of treated fumed silica (pmol/g), which corresponds to an Al:Zr atomic ratio of 100. This gave a spray-dried catalyst of Inventive Example 15, 16, 17, 18, or 19 containing a polymerization catalyst of Inventive Example 6, 10, 11, 12, or 13, respectively.

Inventive Examples 20 to 24: lab-scale polymerization of ethylene and 1-hexene using spray-dried catalyst of any one of Inventive Example 15, 16, 17, 18, or 19 containing a polymerization catalyst of Inventive Example 6, 10, 11, 12, or 13, respectively. Used a 2-liter, stainless steel autoclave gas phase reactor equipped with a mechanical agitator. For each experimental run, first dried the reactor for 1 hour, then charged the dried reactor with 400 g of NaCl and dried by heating at 105° C. under nitrogen for 30 minutes. To the resulting dried reactor, added 5 g of SMAO (silica supported methylalumoxane) as a scavenger under nitrogen pressure. Then sealed the reactor and stirred its contents. Then charged the reactor with hydrogen (1500 ppm) and 1-hexene. Pressurized the reactor with ethylene (total pressure=220 psi) to give H2/C2 molar ratio=0.0017 and C6/C2 molar ratio=0.004. Once the pressurized reactor reached a steady state, charged the spray-dried catalyst of any one of Inventive Example 15, 16, 17, 18, or 19 thereinto to start a polymerization. Brought the reactor temperature to 100° C., and maintained it at this temperature throughout the experiment run for 60 minutes. At 60 minutes, cooled the reactor to room temperature vented and opened. Washed the resulting product mixture with water, then methanol, and dried it to give a poly(ethylene-co-1-hexene) copolymer of any one of Inventive Examples 20 to 24, respectively. Calculated the catalyst activity in grams of polymer made per gram catalyst-hour as equal to a ratio of an amount of polymer yield to the amount of catalyst added to the reactor. Measured number-average molecular weight (Mn), weight average molecular weight (Mw), molecular weight distribution (Mw/Mn), melt temperature, and butyl branch frequency (BBF) according to their foregoing respective test methods. Results are shown below in Table 1.

TABLE 1

Catalysts and copolymers of Inventive Examples 20 to 24.

| Inv. Ex. No. | Catalyst | Catalyst Activity (g copolymer/g catalyst-hour) | Mn | Mw | Mw/Mn | Melt temp. (° C.) | BBF (per 1,000 C) |
|---|---|---|---|---|---|---|---|
| 20 | (8-1) (IE6) | 2,429 | 14,237 | 46,784 | 3.29 | 132.70 | 0.69 |
| 21 | (8-2) (IE10) | 3,311 | 17,998 | 45,438 | 2.52 | 132.44 | 0.6 |
| 22 | (8-3) (IE11) | 10,166 | 11,820 | 38,842 | 3.28 | 130.87 | 1.16 |
| 23 | (8-4) (IE12) | 1,528 | 9,586 | 22,922 | 2.39 | 133.21 | N/d |
| 24 | (8-a1) (IE13) | 2,287 | 12,315 | 32,524 | 2.64 | 133.67 | N/d |

N/d means not detected at a limit of detection (LOD) of 0.1 to 0.2.

As shown in Table 1, the polymerizations of Inventive Examples 20 to 24 using the polymerization catalysts (8-1), (8-2), (8-3), (8-4) and (8a-1) of Inventive Examples 6, 10, 11, 12, and 13, respectively, exhibit ethylene and 1-hexene polymerization activity of at least 1500 grams polymer/gram and produce a poly(ethylene-co-1-hexene) copolymer having a desirable degree of ethylene enchainment as evidence by the molecular weights of the resultant polymers. Each of the copolymers has a weight average molecular weight (Mw) of greater than 20,000, and the copolymers of Inventive Examples 20, 21, 22, 23, and 24 (corresponding to catalysts of Inventive Examples 6, 10, 11, 12 and 13) have butyl branch frequency BBF of less than 1.5, preferably <1. Degree of ethylene enchainment indicates the catalysts selectively permit polymerization of ethylene (i.e., improved ethylene enchainment) while mitigating the polymerization of other molecules such as 1-hexene (e.g., via a particular degree of steric hindrance associated with the substituent groups of the catalysts).

As discussed earlier, Conia et al., Rand and Dolinski, and others report using PPA or $P_2O_5$/PPA mixture to catalyze a reaction of cycloheptene, cyclohexene, or cyclopentene with an alpha,beta-unsaturated carboxylic acid such as acrylic acid or crotonic acid gives a reaction mixture that contains an ester by-product (e.g., cycloheptyl crotonate, cyclohexyl crotonate, or cyclopentyl crotonate, respectively). We found that using a sulfonic acid reagent ($P_2O_5/H_3CSO_3H$ reagent) to catalyze a reaction of cycloheptene, cyclohexene, or cyclopentene with an alpha,beta-unsaturated carboxylic acid such as acrylic acid or crotonic acid gives a reaction mixture that does not contain an ester by-product (e.g., the reaction does not yield cycloheptyl crotonate, cyclohexyl crotonate, or cyclopentyl crotonate, respectively). We base this finding on analysis of at least one of the reaction mixtures by GC/MS (EI), which fails to show any ester by-product. We also base this finding on seeing that the reaction of cycloheptene, cyclohexene, or cyclopentene with an alpha,beta-unsaturated carboxylic acid such as acrylic acid or crotonic acid in the presence of the $P_2O_5/H_3CSO_3H$ reagent goes much faster than a reaction of cycloheptyl crotonate, cyclohexyl crotonate, or cyclopentyl crotonate, respectively, in the presence of the $P_2O_5/H_3CSO_3H$ reagent.

Without wishing to be bound by theory, we believe that the $P_2O_5/H_3CSO_3H$ reagent reacts with the alpha,beta-unsaturated carboxylic acid (e.g., crotonic acid) to give in situ a mixed anhydride of general formula R4CH=CHC(=O)—O—SO$_2$—CH$_3$, which generates in situ an acylium ion (i.e., acyl carbonium ion) of formula R4CH=CHC$^+$(=O), which rapidly undergoes a Friedel-Crafts acylation of cycloalkene to give in situ a ketone of formula R$^a$—C(=O)—R$^c$, wherein R$^a$ is R4CH=CH— and R$^c$ is cycloalken-1-yl, which ketone undergoes cyclization reaction to give the corresponding cyclopentenone. For example, when the cycloalkene is cyclohexene and the alpha,beta-unsaturated carboxylic acid is crotonic acid, we believe that the $P_2O_5/H_3CSO_3H$ reagent reacts with the crotonic acid to give in situ a mixed anhydride of general formula H$_3$CCH=CHC(=O)—O—SO$_2$—CH$_3$, which generates in situ an acylium ion (i.e., acyl carbonium ion) of formula H$_3$CCH=CHC$^+$(=O), which rapidly undergoes a Friedel-Crafts acylation of cycloalkene to give in situ a ketone of formula R$^a$-C(=O)-R$^c$, wherein R$^a$ is H$_3$CCH=CH— and R$^c$ is cyclohexen-1-yl, which ketone undergoes cyclization reaction to give the cyclopentenone that is 2,3,4,5,6,7-hexahydro-3-methyl-1H-inden-1-one (i.e., 7-methyl-bicyclo[4.3.0]-7-nonen-9-one). Therefore, using the $P_2O_5/H_3CSO_3H$ reagent in reaction of a cycloalkene such as cycloheptene, cyclohexene, or cyclopentene with an alpha,beta-unsaturated carboxylic acid such as acrylic acid or crotonic acid does not inherently make the ester by-product (e.g., cycloheptyl crotonate, cyclohexyl crotonate, or cyclopentyl crotonate, respectively) reported by Conia et al., Rand and Dolinski, and others using PPA or $P_2O_5$/PPA mixture.

The invention claimed is:

1. A method of synthesizing a bicyclo[3.3.0]octene compound, the method comprising (A) contacting a compound of formula (1) ("compound (1)"):

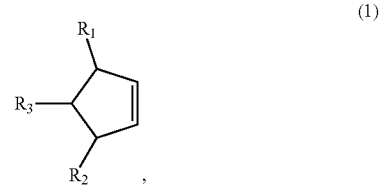

wherein R1, R2, and R3 are independently H or (C$_1$-C$_4$) alkyl, or R1 and R3 are bonded together to form a (C$_1$-C$_4$) alkylene and R2 is H or (C$_1$-C$_4$)alkyl, with a compound of formula (2) ("compound (2)"):

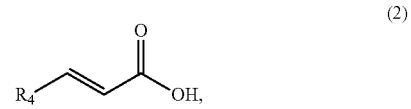

wherein R4 is H or (C$_1$-C$_4$)alkyl, in the presence of an effective amount of a phosphoric and/or sulfonic acid reagent and under reaction conditions sufficient to make a compound of formula (3) ("compound (3)"):

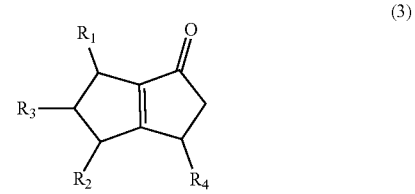

and/or its oxo/R4 regioisomer; wherein R1 to R4 are as defined above.

2. A method of synthesizing a ligand for a transition metal, the method comprising: (A) synthesizing the compound (3):

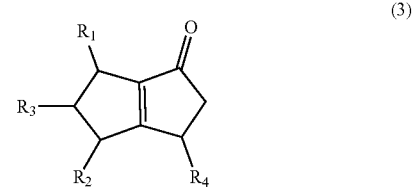

and its oxo/R4 regioisomer, according to step (A) of claim 1, wherein R1 to R4 are as defined in claim 1; (B) contacting the compound (3) and/or its oxo/R4 regioisomer with either a hydride-functional reducing agent or a (C$_1$-C$_4$)alkyl lithium, under reaction conditions sufficient to make a compound of formula (4) ("compound (4)"):

(4)

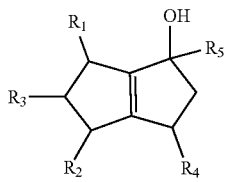

and/or its (HO,R5)/R4 regioisomer, respectively, wherein R1 to R4 are as defined above and R5 is either H or $(C_1-C_4)$alkyl, respectively; and (C) contacting the compound (4) and/or its (HO,R5)/R4 regioisomer with dehydration reaction conditions to make a compound of formula (5) ("compound (5)"):

(5)

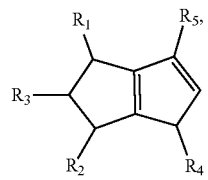

and/or its R5/R4 regioisomer, respectively, wherein the dehydration reaction conditions include temperature and a reagent effective for enhancing rate of loss of water from compound (4) and/or its (HO,R5)/R4 regioisomer; wherein R1 to R5 are as defined above.

3. A method of synthesizing a zirconocene dichloride complex, the method comprising synthesizing the compound (5) and/or its R5/R4 regioisomer according to steps (A) to (C) of claim 2; (D) contacting the compound (5) and/or its R5/R4 regioisomer with an alkyl lithium under reaction conditions sufficient to make a compound of formula (6) ("compound (6)"):

(6)

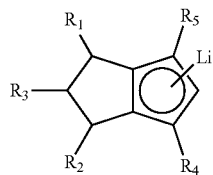

and/or its R5/R4 regioisomer, wherein R1 to R5 are as defined in claim 2; and (E) contacting the compound (6) and/or its R5/R4 regioisomer with a compound of formula (7) ("compound (7)"):

(7)

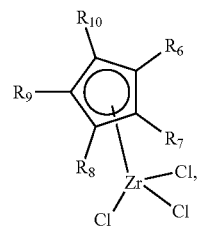

wherein R6 to R8 independently are H or $(C_1-C_4)$alkyl and R9 and R10 independently are H, $(C_1-C_4)$alkyl, or R9 and R10 are bonded together and are a $(C_3-C_5)$alkylene, under reaction conditions sufficient to make a compound of formula (8) ("compound (8)"):

(8)

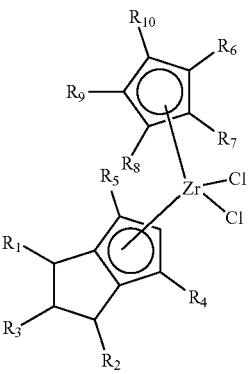

and/or its R5/R4 regioisomer.

4. A method of synthesizing a zirconocene dimethyl complex, the method comprising synthesizing the compound (8) and/or its R5/R4 regioisomer according to steps (A) to (E) of claim 3; and (F) contacting the compound (8) and/or its R5/R4 regioisomer with an effective amount of methyl magnesium bromide under reaction conditions sufficient to make a compound of formula (9) ("compound (9)"):

(9)

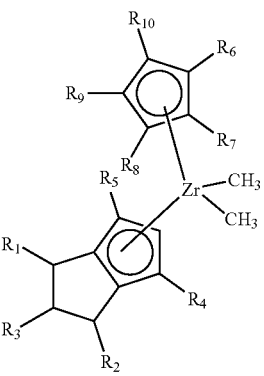

and/or its R5/R4 regioisomer.

5. The method of claim 1, wherein the phosphoric and/or sulfonic acid reagent is a polyphosphoric acid (PPA); a mixture of a phosphorous pentoxide and methanesulfonic acid ("$P_2O_5/H_3CSO_3H$ mixture"), or a reaction product thereof; or a combination of a PPA and a $P_2O_5/H_3CSO_3H$ mixture, or a reaction product of thereof.

6. The method of claim 1 wherein the phosphoric and/or sulfonic acid reagent is a polyphosphoric acid (PPA).

7. The method of claim 1, wherein the phosphoric and/or sulfonic acid reagent is the $P_2O_5/H_3CSO_3H$ mixture, or a reaction product thereof.

8. The method of claim 1, wherein the phosphoric and/or sulfonic acid reagent is the combination of the PPA and the $P_2O_5/H_3CSO_3H$ mixture, or a reaction product thereof.

9. The method of claim 1, characterized by any one of limitations (i) to (ix): (i) wherein at least one of R1 to R3 is a ($C_1$-$C_4$)alkyl or R4 is H; (ii) wherein each of R1 to R4 is H; (iii) wherein each of R1 to R3 is H and R4 is methyl; (iv) wherein in compound (1) each of R2 and R3 is H and R1 is methyl; in compound (2) R4 is methyl; and in compound (3) each of R2 and R3 is H and each of R1 and R4 is methyl; and in its oxo/R4 regioisomer each of R1 and R3 is H and each of R2 and R4 is each methyl; (v) wherein R1 and/or R2 is methyl and R3 is H; (vi) wherein R1 is methyl, R2 is 1-methylethyl (i.e., isopropyl), and R3 is H; (vii) wherein R1 is 1-methylethyl (i.e., isopropyl), R2 is methyl, and R3 is H; (viii) wherein R1 and R2 independently are ($C_1$-$C_4$)alkyl, R3 is H, and the stereochemistry of the carbon atom bonded to R1 is (R) and the stereochemistry to the carbon atom bonded to R2 is (S); and (ix) wherein R1 and R2 independently are ($C_1$-$C_4$)alkyl, R3 is H, and the stereochemistry of the carbon atom bonded to R1 is (S) and the stereochemistry to the carbon atom bonded to R2 is (R).

10. A method of polymerizing an olefin, the method comprising contacting ethylene and/or an alpha-olefin with a catalyst made by contacting the compound (8) or (9), or its R5/R4 regioisomer, made by the method of claim 4, with an activator, under conditions sufficient to make a polyolefin polymer comprising a polyethylene homopolymer, an ethylene/alpha-olefin copolymer, or a poly(alpha-olefin) homopolymer.

* * * * *